(12) United States Patent
Maile et al.

(10) Patent No.: US 10,881,863 B2
(45) Date of Patent: Jan. 5, 2021

(54) LEADLESS CARDIAC PACEMAKER WITH MULTIMODE COMMUNICATION

(71) Applicant: CARDIAC PACEMAKERS, INC., St. Paul, MN (US)

(72) Inventors: Keith R. Maile, New Brighton, MN (US); William J. Linder, Golden Valley, MN (US); Jacob M. Ludwig, Isanti, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 228 days.

(21) Appl. No.: 15/818,311

(22) Filed: Nov. 20, 2017

(65) Prior Publication Data

US 2018/0140853 A1 May 24, 2018

Related U.S. Application Data

(60) Provisional application No. 62/424,947, filed on Nov. 21, 2016.

(51) Int. Cl.
| | | |
|---|---|---|
| *A61N 1/372* | (2006.01) |
| *A61N 1/375* | (2006.01) |
| *A61N 1/02* | (2006.01) |
| *A61N 1/365* | (2006.01) |

(Continued)

(52) U.S. Cl.
CPC ......... *A61N 1/37223* (2013.01); *A61N 1/025* (2013.01); *A61N 1/36514* (2013.01); *A61N 1/36535* (2013.01); *A61N 1/3756* (2013.01); *A61N 1/3787* (2013.01); *A61N 1/37229* (2013.01); *A61N 1/37512* (2017.08); *A61N 1/365* (2013.01); *A61N 1/3754* (2013.01);
(Continued)

(58) Field of Classification Search
CPC .................. A61N 1/3756; A61N 1/37223
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| 4,142,530 A | 3/1979 | Wittkampf |

(Continued)

FOREIGN PATENT DOCUMENTS

| | | |
|---|---|---|
| AU | 2009231721 B2 | 10/2009 |
| AU | 2008279789 B2 | 10/2011 |

(Continued)

OTHER PUBLICATIONS

US 8,886,318 B2, 11/2014, Jacobson et al. (withdrawn)
(Continued)

*Primary Examiner* — Alyssa M Alter
(74) *Attorney, Agent, or Firm* — Seager, Tufte & Wickhem LLP.

(57) ABSTRACT

Implantable medical devices such as leadless cardiac pacemakers may be configured to communicate using more than one mode of communication. For example, in some cases, an implantable medical device may be configured to communicate via conducted communication in some circumstances and to communicate via inductive communication in other circumstances. In some cases, the implantable medical device may be configured to switch between communication modes in order to improve communication.

20 Claims, 18 Drawing Sheets

(51) Int. Cl.
*A61N 1/378* (2006.01)
*A61N 1/39* (2006.01)
(52) U.S. Cl.
CPC ...... *A61N 1/37205* (2013.01); *A61N 1/37217* (2013.01); *A61N 1/3956* (2013.01)

(56) References Cited

U.S. PATENT DOCUMENTS

| | | |
|---|---|---|
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,871,625 A | 2/1999 | Leddy et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,804 A | 7/1999 | Leddy et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,981,095 A | 11/1999 | Leddy et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |

(56) References Cited

U.S. PATENT DOCUMENTS

| | | |
|---|---|---|
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,207,313 B1 | 3/2001 | Leddy et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,322,676 B1 | 11/2001 | Leddy et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,355,166 B1 | 3/2002 | Amarasinghe et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,479,176 B2 | 11/2002 | Leddy et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,766,200 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,890,670 B2 | 5/2005 | Leddy et al. |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |

(56) References Cited

U.S. PATENT DOCUMENTS

| | | | |
|---|---|---|---|
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,225,032 B2 | 5/2007 | Schmeling et al. |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 * | 7/2009 | Kroll ................ A61N 1/37288 607/2 |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |

(56) References Cited

U.S. PATENT DOCUMENTS

| | | |
|---|---|---|
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,140,168 B2 | 3/2012 | Olson et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,322 B2 | 10/2013 | Olson et al. |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,630,717 B2 | 1/2014 | Olson et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |

(56) References Cited

U.S. PATENT DOCUMENTS

| | | |
|---|---|---|
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 * | 12/2015 | Boling .................. A61N 1/059 |
| 9,216,293 B2 | 12/2015 | Berthiaume et al. |
| 9,216,297 B2 | 12/2015 | Kast et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,333,365 B2 | 5/2016 | Zhao |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,405 B2 | 7/2016 | Hastings et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,431,694 B2 | 8/2016 | Li et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |

(56) References Cited

U.S. PATENT DOCUMENTS

| | | |
|---|---|---|
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0071328 A1 | 3/2008 | Haubrich et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0262573 A1 | 10/2008 | Seeberger et al. |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0066211 A1 | 3/2011 | Von Arx et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |

(56) References Cited

U.S. PATENT DOCUMENTS

| | | |
|---|---|---|
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |

(56) References Cited

U.S. PATENT DOCUMENTS

| | | |
|---|---|---|
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0309706 A1 | 10/2014 | Jacobson |
| 2014/0350652 A1 | 11/2014 | Suwito et al. |
| 2014/0379041 A1 | 12/2014 | Foster |
| 2015/0018728 A1 | 1/2015 | Gross et al. |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0224323 A1 | 8/2015 | Chen et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0059022 A1 | 3/2016 | Stahmann et al. |
| 2016/0101291 A1 | 4/2016 | Jaax et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2008329620 B2 | 5/2014 |
| AU | 2014203793 A1 | 7/2014 |
| CA | 1003904 A1 | 1/1977 |
| CA | 2679413 C | 9/2008 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| EP | 2398556 B1 | 8/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016149262 A1 | 9/2016 |
| WO | 2017044904 A1 | 3/2017 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(384): 324-331, 1970.

"Instructions for Use System 1, Leadless Cardiac Pacemaker (LCP) and Delivery Catheter," Nanostim Leadless Pacemakers, pp. 1-28, 2013.

(56) References Cited

OTHER PUBLICATIONS

Invitation to Pay Additional Fees and, Where Applicable, Protest Fee for Application No. PCT/US2017/062594, 12 pages, date mailed Mar. 19, 2018.

* cited by examiner

LEADLESS CARDIAC PACEMAKER WITH MULTIMODE COMMUNICATION

CROSS REFERENCE TO RELATED APPLICATIONS

This application claims the benefit of U.S. Provisional Patent Application Ser. No. 62/424,947 filed on Nov. 21, 2016, the disclosure of which is incorporated herein by reference.

TECHNICAL FIELD

The present disclosure pertains to medical devices, and more particularly to implantable medical devices such as leadless cardiac pacemakers that can communicate with other devices.

BACKGROUND

Implantable medical devices are commonly used today to monitor physiological or other parameters of a patient and/or deliver therapy to a patient. For example, to help patients with heart related conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In another example, neuro stimulators can be used to stimulate tissue of a patient to help alleviate pain and/or other condition. In yet another example, an implantable medical device may simply be an implantable monitor that monitors one or more physiological or other parameters of the patient, and communicates the sensed parameters to another device such as another implanted medical device or an external device. In some cases, two or more devices cooperate to monitor and/or to provide therapy. In many of these examples, there is a desire to have such devices communicate with other devices when needed.

SUMMARY

This disclosure describes implantable medical devices (IMD), such as but not limited to leadless cardiac pacemakers (LCP), neuro-stimulators (NS), and/or implantable monitors (IM), that are configured to communicate using more than one mode of communication. For example, an implantable medical device may be configured to communicate via conducted communication in some circumstances and to communicate via inductive communication in other circumstances. In some cases, the implantable medical device may be configured to switch between communication modes, which may help improve communication reliability and/or communication speed between devices.

In one example, a leadless cardiac pacemaker (LCP) is configured to pace a patient's heart from within a chamber of the patient's heart. The LCP may include a housing and a plurality of electrodes that are secured relative to the housing. Two or more inductive coils may be secured relative to the housing and may each include a plurality of windings extending about a central axis, wherein the central axis of one of the two or more inductive coils is not parallel with the central axis of another one of the two or more inductive coils. A controller may be disposed within the housing and may be operably coupled to the plurality of electrodes and the two or more inductive coils. The controller may be configured to sense cardiac electrical activity of the patient's heart via two or more of the electrodes and to generate and deliver pacing pulses via two or more of the electrode. In some cases, the controller may be configured to communicate with one or more remotely located devices using conducted communication via two or more of the electrodes and inductive communication via one or more of the two or more inductive coils.

Alternatively or additionally to any of the embodiments above, the controller may be configured to select a particular one of the two or more inductive coils for inductive communication, and to communicate with one or more remotely located devices using inductive communication via the selected one of the two or more inductive coils, while not using the non-selected ones of the two or more inductive coils for inductive communication.

Alternatively or additionally to any of the embodiments above, the controller may be configured to select two or more of the inductive coils for inductive communication, and to communicate with one or more remotely located devices using inductive communication via the selected two or more inductive coils.

Alternatively or additionally to any of the embodiments above, at least one of the two or more inductive coils may be disposed within the housing.

Alternatively or additionally to any of the embodiments above, the controller may be configured to disable inductive communication to save power and communicate with one or more remotely located devices using conducted communication. The controller may be configured to detect a predetermined condition, and in response to detecting the predetermined condition, enable inductive communication and communicate with one or more remotely located devices using inductive communication.

Alternatively or additionally to any of the embodiments above, the controller may include a time clock, and the predetermined condition may include a predetermined time of day.

Alternatively or additionally to any of the embodiments above, the LCP may further include a posture sensor for detecting a posture of the patient and the predetermined condition may include detection of a predetermined posture of the patient.

Alternatively or additionally to any of the embodiments above, the predetermined condition may include an error in conducted communication with one or more remotely located devices.

Alternatively or additionally to any of the embodiments above, the controller may be further configured to have a fail-safe in which a user is prevented from having conductive communication and inductive communication disabled at the same time.

In another example, a leadless cardiac pacemaker (LCP) is configured to pace a patient's heart from within a chamber of the patient's heart. The LCP may include an elongated housing having a length dimension and a width dimension, wherein the length dimension is longer than the width dimension. A plurality of electrodes may be secured relative to the elongated housing and a plurality of internal components may be disposed within the elongated housing. The plurality of internal components may include an inductive coil that is disposed within the elongated housing and that includes a plurality of windings extending about a central aperture aligned in the direction of the length dimension of the elongated housing. The plurality of internal components may include a circuit board including circuitry that is operably coupled to the plurality of electrodes and that is configured to sense cardiac electrical activity of the patient's heart via two or more of the electrodes and to generate and deliver pacing pulses via two or more of the electrodes. In some cases, the circuitry may be further configured to communicate with one or more remotely located devices using conducted communication via two or more of the electrodes and using inductive communication via the inductive coil. A battery may be disposed within the elongated housing and may be operably coupled to the circuitry. At least part of one or more of the internal components of the LCP may extend into and occupy at least part of the central aperture of the inductive coil.

Alternatively or additionally to any of the embodiments above, the inductive coil has a length extending along the length dimension of the elongated housing and a width orthogonal to the length, wherein a ratio of the length of the inductive coil to the width is less than one.

Alternatively or additionally to any of the embodiments above, the plurality of internal components within the elongated housing may include a battery pin extending between a terminal of the battery and circuitry of the circuit board, wherein the battery pin extends through and occupies at least part of the central aperture of the inductive coil.

Alternatively or additionally to any of the embodiments above, the plurality of internal components within the elongated housing may include a feed through pin extending between circuitry of the circuit board and one of the plurality of electrodes, wherein the feed through pin extends through and occupies at least part of the central aperture of the inductive coil.

Alternatively or additionally to any of the embodiments above, the LCP may further include a second inductive coil that is disposed within the elongated housing and that includes a plurality of windings extending about a central aperture, wherein the central aperture of the second inductive coil extends in the direction of the width dimension of the elongated housing.

Alternatively or additionally to any of the embodiments above, the central aperture of the second inductive coil may extend parallel with the circuit board or perpendicular to the circuit board.

Alternatively or additionally to any of the embodiments above, the second inductive coil may have a length that extends in the direction of the width dimension of the elongated housing, and a width that is orthogonal to the length, wherein a ratio of the length of the inductive coil to the width is greater than three, and wherein the second inductive coil comprises a ferrite core in the central aperture of the second inductive coil.

In another example, a leadless cardiac pacemaker (LCP) is configured to pace a patient's heart from within a chamber of the patient's heart. The LCP may include an elongated housing having a length dimension and a width dimension, wherein the length dimension is longer than the width dimension, and a plurality of electrodes that are secured relative to the elongated housing. A circuit board assembly may include two or more stacked circuit boards that are operably coupled together via flexible interconnects and may be disposed within the elongated housing such that each of the two or more stacked circuit boards are orthogonal to the length dimension of the elongated housing. The circuit board assembly may include circuitry that is operably coupled to the plurality of electrodes and that is configured to sense cardiac electrical activity of the patient's heart via two or more of the electrodes and to generate and deliver pacing pulses via two or more of the electrodes. An inductive coil may be disposed within the elongated housing such that the inductive coil extends between a first circuit board and a second circuit board of the plurality of circuit boards. The circuitry may be configured to communicate with one or more remotely located devices using conducted communication via two or more of the electrodes and inductive communication via the inductive coil.

Alternatively or additionally to any of the embodiments above, the LCP may further include a second inductive coil that is disposed within the elongated housing such that the second inductive coil extends between two of the plurality of circuit boards of the plurality of circuit boards.

Alternatively or additionally to any of the embodiments above, the LCP may further include a second inductive coil that is disposed within the elongated housing and is arranged orthogonal to the inductive coil.

Alternatively or additionally to any of the embodiments above, the LCP may further include a third inductive coil that is disposed within the elongated housing and is arranged orthogonal to both the inductive coil and the second inductive coil.

The above summary of some illustrative embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
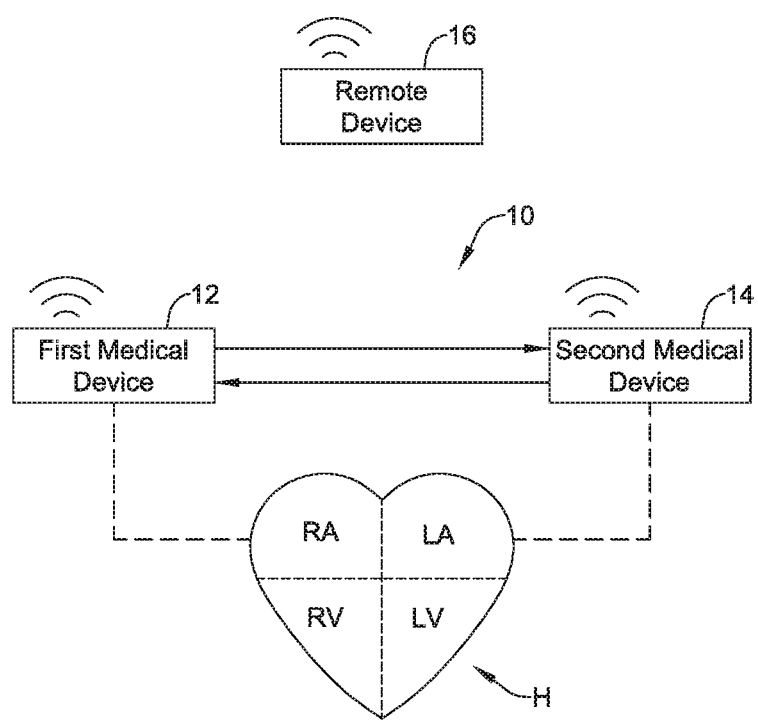
FIG. 1 is a highly schematic diagram of an illustrative system in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure. While the present disclosure is applicable to any suitable implantable medical device (IMD), the description below uses pacemakers and more particularly leadless cardiac pacemakers (LCP) as particular examples.

FIG. 1 is a schematic diagram showing an illustrative system 10 that may be used to sense and/or pace a heart H.

In some cases, the system 10 may also be configured to shock the heart H. The heart H includes a right atrium RA and a right ventricle RV. The heart H also includes a left atrium LA and a left ventricle LV. In some cases, the system 10 may include a medical device that provides anti-arrhythmic therapy to the heart H.

In some cases, the system 10 may include a first medical device 12 and a second medical device 14. The first medical device 12 may be any suitable medical device such as a leadless cardiac pacemakers (LCP), an implantable cardioverter defibrillator (ICD), an implantable neuro-stimulator (NS), an implantable monitor (IM), an external programmer, and/or any other suitable medical device. Likewise, the second medical device 14 may be any suitable medical device such as a leadless cardiac pacemakers (LCP), an implantable cardioverter defibrillator (ICD), an implantable neuro-stimulator (NS), an implantable monitor (IM), an external programmer, and/or any other suitable medical device.

In some instances, the first medical device 12 may be implantable within the patient at a position near or even within the heart H. In some cases, the second medical device 14 may be implanted within the patient but at a location that is exterior to the heart H. For example, in some cases, the second medical device 14 may be implanted at a subcutaneous position within the patient's chest. In some cases, the system 10 may include a remote device 16. The remote device 16 may be a monitor or a programmer, for example.

In some cases, the first medical device 12 may be configured to sense electrical cardiac activity of the heart H and provide therapeutic electrical pulses to the heart H. In some cases, the second medical device 14 may be configured to sense electrical cardiac activity of the heart H and provide therapeutic electrical pulses to the heart H. In some cases, the first medical device 12 may be a leadless cardiac pacemaker (LCP) and may be configured to provide pacing pulses to the heart H. The second medical device 14 may be a second LCP. In some cases, the second medical device 14 may be a subcutaneous implantable cardioverter defibrillator (SICD) and may be configured to provide shocking pulses to the heart H.

In some cases, if the second medical device 14 is implanted prior to implanting the first medical device 12, the second medical device 14 may be used to guide optimal placement of the first medical device 12, for example, by monitoring the QRS width, morphology, HRV, accelerometer signals, etc. In some cases, the second medical device 14 may provide feedback of a proposed first medical device's 12 location prior to fixation or untethering of the first medical device 12. Minimizing QRS width, HRV and/or certain morphological parameters would be a possible goal of the clinician to obtain such an optimal site, for example. In some cases, the second medical device 14 may also be able to monitor the impedance and or heart sounds to possibly detect myocardial functional improvements as indicated by hyperthoprhy or dilated cardiomyopathy.

In some cases, the first medical device 12 and the second medical device 14 may be implanted at the same time. In some instances, depending on the cardiac deficiencies of a particular patient, one of the first medical device 12 and the second medical device 14 may be implanted first, and the other of the first medical device 12 and the second medical device 14 may be implanted at a later date if/when the patient develops indications for receiving cardiac resynchronization therapy and/or it becomes necessary to pace the heart H. In some cases, it is contemplated that one or more LCPs may be implanted first, in order to sense and pace the heart H. When a need for possible defibrillation becomes evident, an SICD may subsequently be implanted.

Regardless of implantation order or sequence, it will be appreciated that the first medical device 12 and the second medical device 14 may communicate with each other, as well as with the remote device 16, using any desired communications modality, such as conducted communication, inductive communication, acoustic communication, RF communication, optical communication and/or using any other suitable communication modality. In some cases, a medical device such as the first medical device 12 and/or the second medical device 14 may be configured to communicate using two or more different communication modes. It will be appreciated that different communication modes may have different power requirements, effective communication ranges, and the like. In some cases, a medical device may communication with a first communication mode having relatively lower power requirements when the first communication mode is effective and may switch to a second communication mode having relatively higher power requirements when the first communication mode loses effectiveness, for example.

In some cases, a medical device may select a particular communication mode based upon the identity and/or location of another device. For example, if the first medical device 12 and the second medical device 14 are both implanted within a patient, the first medical device 12 and the second medical device 14 may communicate with each other via conducted communication, assuming there is a workable communication vector between the first medical device 12 and the second medical device 14. In some cases, such as if the first medical device 12 (or the second medical device 14) is attempting to communicate with the remote device 16, the possible use of conducted communication would require the remote device 16 to be operably coupled with two or more skin electrodes disposed on the patient (e.g. via skin patch electrodes). Instead, the first medical device 12 (or the second medical device 14) may terminate conducted communication and may attempt to communicate with the remote device 16 via inductive communication, which would not require the use of skin electrodes.

Figure 2:
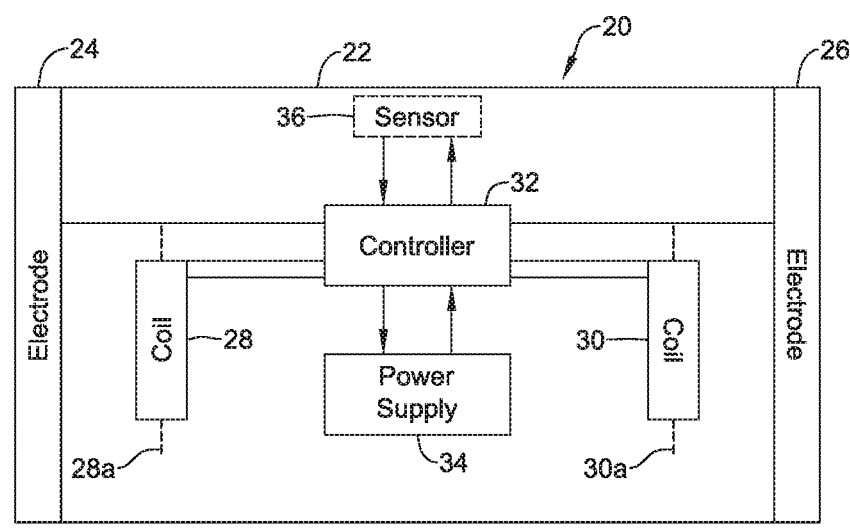
FIG. 2 is a schematic block diagram of an illustrative leadless cardiac pacemaker (LCP) in accordance with an example of the disclosure.

FIG. 2 is a schematic block diagram of an illustrative leadless cardiac pacemaker (LCP) 20 that may be configured to be disposable within a chamber of the patient's heart H and pace the patient's heart. The illustrative LCP 20 may include a housing 22 and a plurality of electrodes that are secured relative to the housing 22. As illustrated, the LCP 20 includes a first electrode 24 and a second electrode 26, although in some cases the LCP 20 may include additional electrodes as well. In some cases, the LCP 20 may include one, two, or more inductive coils. In some cases, the LCP 20 may include an RF antenna, if desired.

Figure 4:
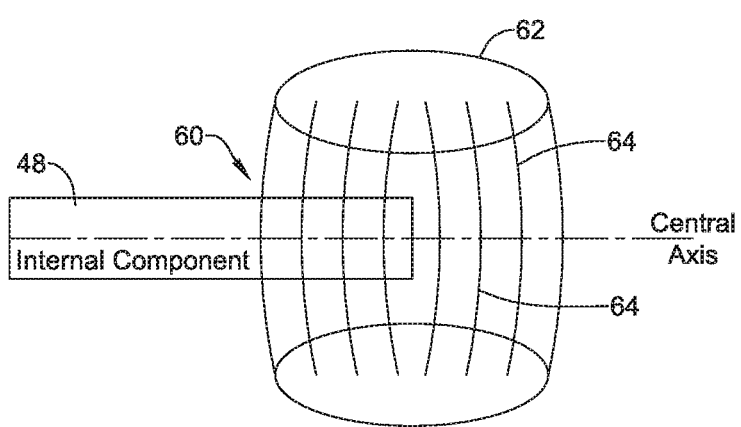
FIG. 4 is a schematic illustration of a portion of the LCP of FIG. 3.

As illustrated, the LCP 20 includes a first inductive coil 28 and a second inductive coil 30, each of which include a plurality of windings (as will be illustrated in FIGS. 4B and 5B) each extending about a corresponding central axis. The first inductive coil 28 is shown as having a central axis 28a and the second inductive coil 30 is shown as having a central axis 30a. In some cases, the central axis 28a of the first inductive coil 28 is not parallel with the central axis 30a of the second inductive coil 30. In some cases, as shown, the central axis 28a may be orthogonal to the central axis 30a. In some cases, at least one of the first inductive coil 28 and the second inductive coil 30 may be disposed within the housing 22. In some instances, at least one of the first inductive coil 28 or the second inductive coil 30, or optionally an additional coil, may include a winding disposed on a flexible substrate that curves around a curved inside surface of a housing of the LCP 20.

In some cases, the LCP 20 may include a third inductive coil (not illustrated). The third inductive coil, if included, may be orthogonal to one of the first inductive coil 28 and the second inductive coil 30, and may be parallel to the other of the first inductive coil 28 and the second inductive coil 30. In some cases, the third inductive coil, if present, may be orthogonal to both the first inductive coil 28 and the second inductive coil 30. For example, one inductive coil may have a central axis aligned with an x axis, another inductive coil may have a central axis aligned with a y axis and a third inductive coil may have a central axis aligned with a z axis. This is merely an example.

The LCP 20 may include a controller 32 that is disposed within the housing 22 and may be operably coupled to the plurality of electrodes, such as but not limited to the first electrode 24 and the second electrode 26, as well as to the two or more inductive coils, such as but not limited to the first inductive coil 28 and the second inductive coil 30. A power supply 34 may be operably coupled to the controller 32 and may provide electrical power for operation of the controller 32 as well as other functionality of the LCP 20. In some cases, the controller 32 may be configured to sense cardiac electrical activity of the patient's heart H via the first electrode 24 and the second electrode 26 (and optionally other electrodes) and to generate and deliver pacing pulses via the first electrode 24 and the second electrode 26.

In some cases, the controller 32 may be configured to communicate with one or more remotely located devices (such as but not limited to the remote device 16 shown in FIG. 1) using conducted communication via the first electrode 24 and the second electrode 26, and using inductive communication via at least one of the first inductive coil 28 and the second inductive coil 30. In some cases, the controller 32 may be configured to select a particular one of the two or more inductive coils (such as the first inductive coil 28 or the second inductive coil 30) for inductive communication, and to communicate with one or more remotely located devices using inductive communication via the selected one of the two or more inductive coils, while not using the non-selected ones of the two or more inductive coils for inductive communication. In some cases, the controller 32 may be configured to select two or more of the inductive coils for inductive communication, and to communicate with one or more remotely located devices using inductive communication via the selected two or more inductive coils.

In some cases, the controller 32 may be configured to disable inductive communication to save power and instead communicate with one or more remotely located devices (such as the remote device 16) using conducted communication. If a predetermined condition is detected, the controller 32 may, in response, enable inductive communication and communicate with one or more remotely located devices using inductive communication in order to help ensure a viable communication path. In some cases, the controller 32 may include functionality of a time clock, and the predetermined condition may be a predetermined time of day, for example. For example, the remote device 16 may be a bedside monitor, and the predetermined time of day may correspond to a patient's bedtime. Inductive communication may be activated at a time when the patient is expected to be in bed (e.g. midnight) so that the LCP 20 may communicate with the remote device 16. In some cases, the LCP 20 may include a sensor 36, such as but not limited to, a posture sensor. When so provided, the predetermined condition may be a predetermined posture of the patient. For example, if the sensor 36 detects that the patient is laying down, the controller 32 may activate inductive communication to communicate with a bedside monitor. In some cases, a predetermined condition that causes the controller 32 to activate inductive communication may correspond to a detected error during conducted communication with one or more remotely located devices. This may include a transient communication error, or an extended loss of communication. This may also include when conducted communication is able to communicate some information, but with an unacceptable loss of data. These are just examples.

In some cases, the controller 32 may be configured to have a fail-safe in which a user is prevented from having conductive communication and inductive communication disabled at the same time. This may help prevent a possible situation in which the user accidently or unknowingly instructs the controller 32 to stop conducted communication as well as stop inductive communication, as this could leave the user with no effective way to communicate with the LCP 20.

In some cases, the controller 32 may be configured to receive near field energy from another device via one or more of the first inductive coil 28 and the second inductive coil 30 (or another coil), and use the received near field energy to charge the power supply 34. The controller 32 may receive the near field energy and recharge the power supply 43 when the corresponding inductive coil is not being used for communication.

Figure 3:
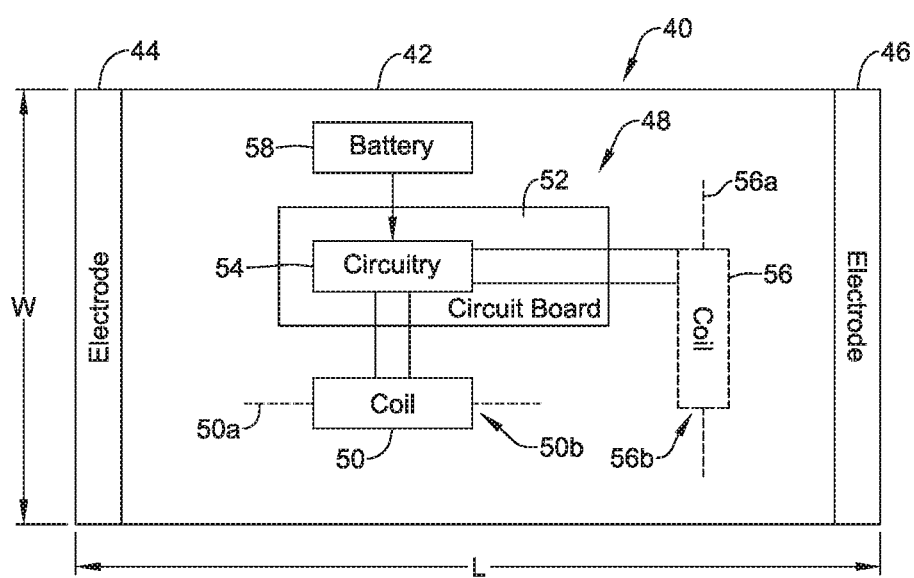
FIG. 3 is a schematic block diagram of an illustrative leadless cardiac pacemaker (LCP) in accordance with an example of the disclosure

FIG. 3 is a schematic block diagram of an illustrative leadless cardiac pacemaker (LCP) 40 that may be configured to be disposable within a chamber of the patient's heart H and to pace the patient's heart. The LCP 40 may include an elongated housing 42 having a length dimension denoted by L and a width dimension denoted by W. In some cases, the length dimension L may be longer than the width dimension W. A plurality of electrodes may be secured relative to the elongated housing 42. As illustrated, the LCP 40 includes a first electrode 44 and a second electrode 46, although in some cases the LCP 40 may include additional electrodes as well. In some cases, the LCP 40 may include a plurality of internal components 48 within the elongated housing 42.

In some instances, the plurality of internal components 48 may include an inductive coil 50 that is disposed within the elongated housing 42 and that includes (as will be shown in FIGS. 5A and 6A) a plurality of windings extending about a central aperture 50b that corresponds to a central axis 50a and that is aligned in the direction of the length dimension L of the elongated housing 42. In some cases, the plurality of internal components 48 may include a circuit board 52 including circuitry 54 that is operably coupled to the plurality of electrodes such as the first electrode 44 and the second electrode 46 (and optionally one or more additional electrodes) and that is configured to sense cardiac electrical activity of the patient's heart H via two or more of the electrodes 44, 46 and to generate and deliver pacing pulses via two or more of the electrodes 44, 46. In some cases, the LCP 40 may further include a first inductive coil 50 having a plurality of windings extending about a central aperture 50b that corresponds to a central axis 50a and that is parallel to the length dimension L of the elongated housing 42. In some cases, the LCP 40 may further include a second inductive coil 56 having a plurality of windings extending about a central aperture 56b that corresponds to a central axis 56a and that is orthogonal the length dimension L of the elongated housing 42. In some cases, the circuitry 54 may be configured to communicate with one or more remotely located devices (such as the remote device 16 of FIG. 1) using conducted communication via two or more of the electrodes and/or inductive communication via the first inductive coil 50 and/or second inductive coil 56. A battery 58 may be disposed within the elongated housing 42 and may be operably coupled to the circuitry 54.

In some cases, at least part of one or more of the internal components 48 may extend at least partially into and may occupy at least part of the central aperture 50b of the inductive coil 50 and/or the central aperture 56b of the inductive coil 56. This may be seen schematically in FIG. 4, which shows a portion of the plurality of internal components 48 extending into a central aperture 60 of an inductive coil 62. As illustrated, it may be seen that the inductive coil 62 includes a plurality of windings 64 that extend vertically (in the illustrated orientation). In some cases, one or more of the internal components 48 may extend at least partially into the central aperture 60. In some cases, all or a portion of the circuit board 52 (FIG. 3), part of the battery 58, a terminal pin or connector, a sensor such as an accelerometer, gyroscope, pressure sensor, and/or temperature sensor, and/or any other suitable internal component may extend into the central aperture 60 of the inductive coil 62. In some cases, one or more internal components may extend all the way through the central aperture 60. These are just examples.

Figure 5A:
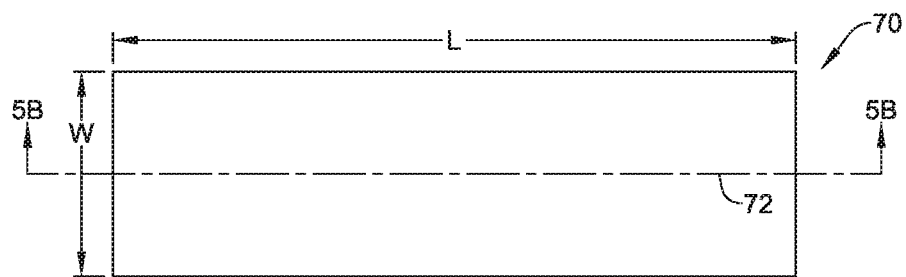
FIG. 5A is a side view of an inductive coil useable in the LCPs of FIGS. 1-3.
Figure 5B:
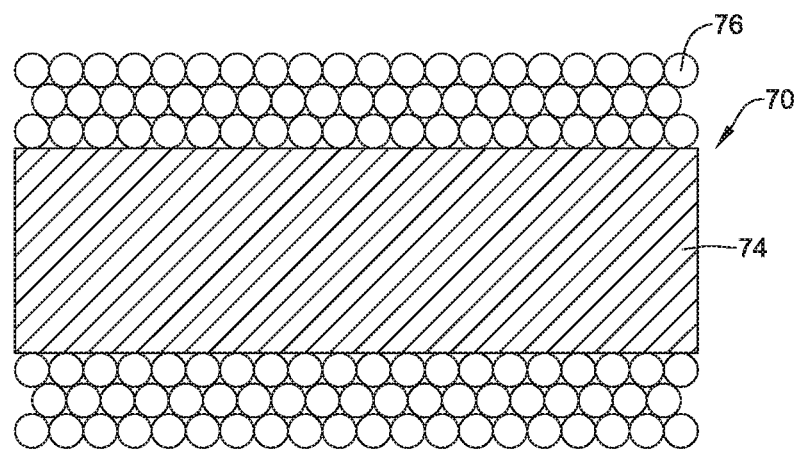
FIG. 5B is a cross-sectional view of the inductive coil of FIG. 5A.

The inductive coils referenced herein may take any suitable form. FIG. 5A is a schematic view of an illustrative inductive coil 70, while FIG. 5B is a cross-sectional view of the inductive coil 70. As can be seen, the inductive coil 70 may be considered as having a length denoted as L and a width denoted as W. In some cases, the width W may be considered as being measured in a direction that is orthogonal to the direction used in measuring the length. The length L may extend perpendicular or substantially perpendicular to the windings of the inductive coil 70, while the width W may extends parallel or substantially parallel to the windings of the inductive coil 70.

The illustrative inductive coil 70 may be considered as having a longitudinal axis 72 that extends through the windings of the inductive coil 70. The length L may, for example, be measured in a direction parallel to the longitudinal axis 72. In some cases, the inductive coil 70 may have a length to width ratio, indicated as L/W, which is greater than 1, i.e., the inductive coil 70 is longer in the length direction L than in the width direction W. In some cases, the inductive coil 70 may have an L/W ratio that is greater than or equal to 2. In some instances, the inductive coil 70 may have an L/W ratio that is greater than or equal to 3. In some cases, the inductive coil 70 may have an L/W ratio that is greater than 4, greater than 5, or larger.

In some cases, the inductive coil 70 may have a core 74. In some cases, core 74 may simply provide a structure for a plurality of windings 76 to be wound around about, and may in some cases actually represent a void (e.g. air). In some cases, particularly if the inductive coil 70 has an L/W ratio of 3 or greater, the core 74 may be a core of magnetically active material such as ferrite. The use of a magnetically active material such as ferrite may provide performance advantages to the inductive coil 70. In some cases, a magnetically active core, whether solid or tubular, may help concentrate magnetic flux through the windings 76 of the inductive coil 70. It will be appreciated that the overall dimensions of the inductive coil 70 will be a function of the dimensions of the core 74 as well as the number of windings 76. The voltage produced by the inductive coil 70 may be proportional to the magnetic field flux passing through the inductive coil 70 and the number of windings 76. The overall dimensions of the inductive coil 70 may be limited by the dimensions of the medical device in which the inductive coil 70 is to be employed, as well as being able to fit the inductive coil 70 in with other components within the medical device.

Figure 6:
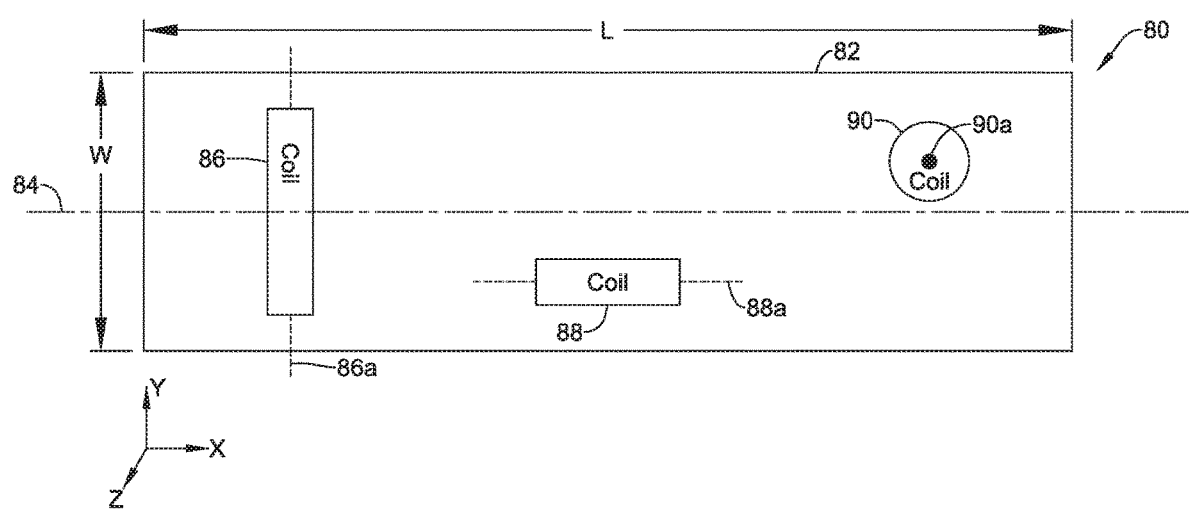
FIG. 6 is a schematic block diagram of an illustrative leadless cardiac pacemaker (LCP) in accordance with an example of the disclosure.

It will be appreciated that an inductive coil may have spatial and/or temporal nulls in which no or virtually no signal may be obtained. In some cases, these nulls are at least partially a function of the orientation of the inductive coil relative to a received magnetic field. Accordingly, in some cases, it may be advantageous to use two or more inductive coils that are arranged at angles relative to each other. FIG. 6 is a schematic diagram of a leadless cardiac pacemaker (LCP) 80 that may include one or more inductive coils, such as the inductive coil 70 shown in FIGS. 5A and 5B. The illustrative LCP 80 includes a housing 82 having a length L and a width W, with the length L measured parallel to a longitudinal axis 84 and the width W measured orthogonal to the longitudinal axis 84. As illustrated, the LCP 80 includes a first inductive coil 86, a second inductive coil 88 and a third inductive coil 90. In this, first, second and third are merely used to denote distinct coils and is not intended to imply anything regarding relative importance of the individual coils, the order in which they may be used, or anything of the like.

The first inductive coil 86 may be seen as having a central axis 86a, the second inductive coil 88 may be seen as having a central axis 88a and the third inductive coil 90 may be seen as having a central axis 90a (extending in/out of the paper) shown here as a point. In some cases, the first inductive coil 86 may be disposed within the housing 82 with its central axis 86a aligned in a y direction. The second inductive coil 88 may be disposed within the housing 82 with its central axis 88a aligned in an x direction. The third inductive coil 90 may be disposed within the housing 82 with its central axis 90a aligned in a z direction. In some cases, the inductive coils 86, 88 and 90 may not all be orthogonal to each other, but may be disposed relative to each other in acute angles less than 90 degrees. In some cases, the first inductive coil 86 may be considered as being disposed within the housing 82 with its central axis 86a parallel to the width W of the housing 82. The second inductive coil 88 may, for example, be considered as being disposed within the housing 82 with its central axis 88a parallel to the length L of the housing 82. In some cases, the LCP 80 may not include all three of the inductive coils 86, 88, 90.

Figure 7A:
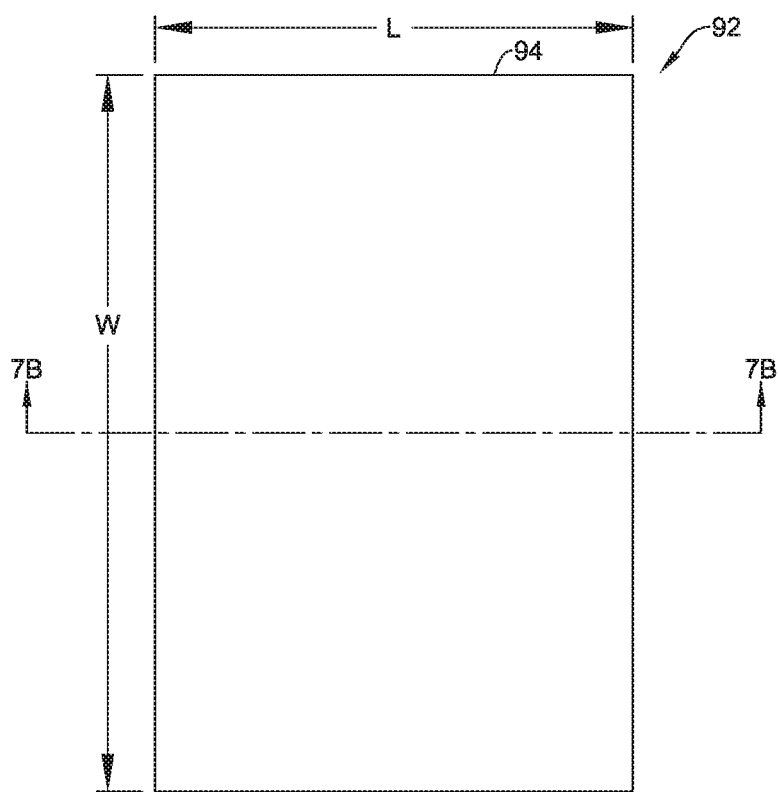
FIG. 7A is a side view of an inductive coil useable in the LCPs of FIGS. 1-3.
Figure 7B:
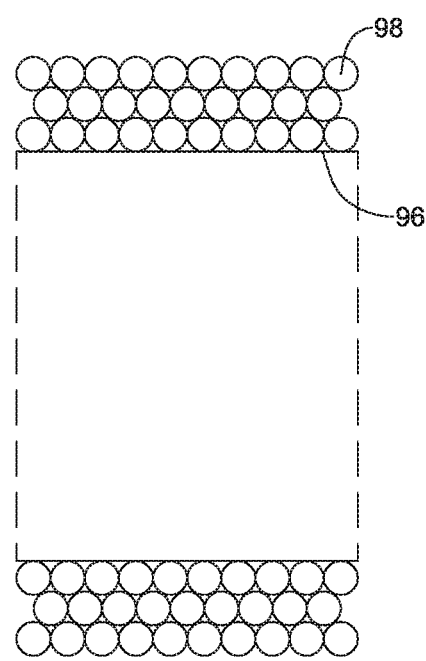
FIG. 7B is a cross-sectional view of the inductive coil of FIG. 7B.

FIG. 7A is a schematic view of another example of an inductive coil 92, while FIG. 7B is a cross-sectional view of the inductive coil 92. As can be seen, the inductive coil 92 may be considered as having a length denoted as L and a width denoted as W. In some cases, the width W may be considered as being measured in a direction that is orthogonal to the direction used in measuring the length. The length L may extend perpendicular or substantially perpendicular to the windings of the inductive coil 70, while the width W may extends parallel or substantially parallel to the windings of the inductive coil 70.

In some cases, the inductive coil 92 may have a length to width ratio, indicated as L/W, that is equal to or less than 1, i.e., the inductive coil 70 is longer in the width direction W than in the length direction L. In some cases, the inductive coil 92 may have an L/W ratio that is less than or equal to 0.75. In some instances, the inductive coil 92 may have an L/W ratio that is less than or equal to 0.5. In some cases, the inductive coil 92 may have an L/W ratio that is less than 0.25.

Figure 8:
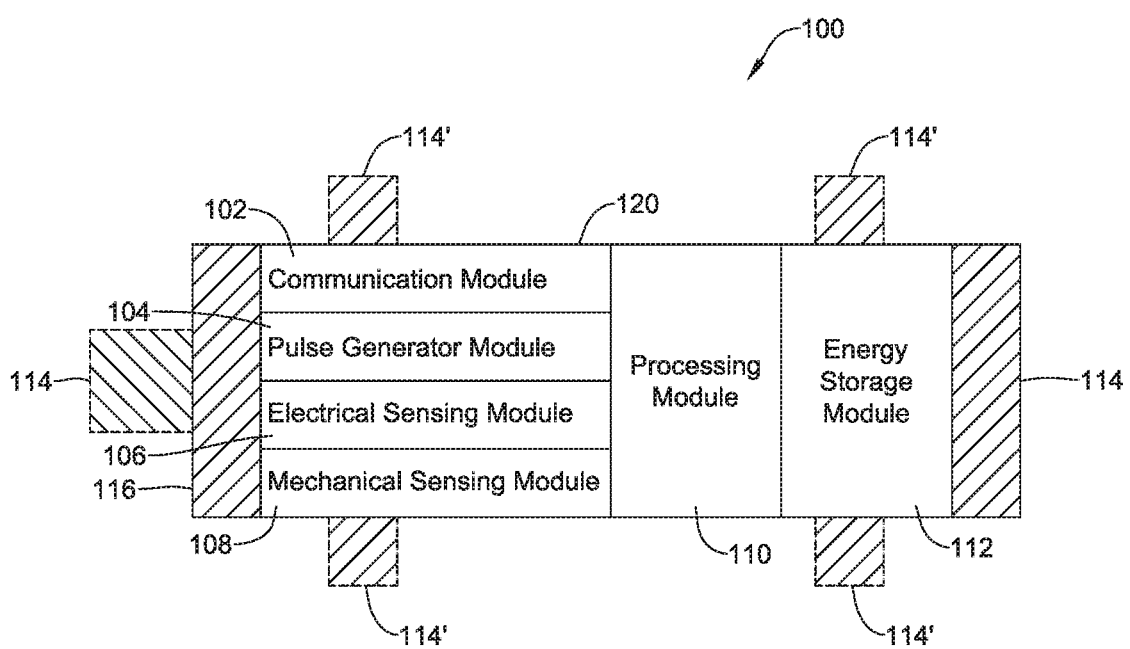
FIG. 8 is a schematic block diagram of an illustrative LCP in accordance with an example of the disclosure.

In some cases, the inductive coil 92 may have a support structure 96 (see FIG. 7B). In some cases, the support structure 96 may simply provide a structure for a plurality of windings 98 to be wound around, and may in some cases be a hollow tube made of any suitable material. It will be appreciated that the overall dimensions of the inductive coil 92 will be a function of the dimensions of the support structure 96 as well as the number of windings 98. The voltage produced by the inductive coil 92 may be proportional to the magnetic field flux passing through the inductive coil 92 and the number of windings 98. The overall dimensions of the inductive coil 92 may be limited by the dimensions of the medical device in which the inductive coil 92 is to be employed, as well as being able to fit the inductive coil 92 in with other components within the medical device. FIG. 8 provides further details pertaining to an example medical device in which an inductive coil, such as the inductive coils 70 and 92, may be used.

FIG. 8 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. The LCP shown in FIG. 8 may include the features described herein for switching between multiple communication modes. As can be seen in FIG. 8, the LCP 100 may be a compact device with all components housed within the or directly on a housing 120. In some cases, the LCP 100 may be considered as being an example of the LCP 20 (FIG. 2), the LCP 40 (FIG. 3) or the LCP 80 (FIG. 6). In the example shown in FIG. 8, the LCP 100 may include a communication module 102, a pulse generator module 104, an electrical sensing module 106, a mechanical sensing module 108, a processing module 110, a battery 112, and an electrode arrangement 114. The LCP 100 may include more or less modules, depending on the application.

The communication module 102 may be configured to communicate with devices such as sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more modes for communicating with external devices. For example, the communication module 102 may communicate via radiofrequency (RF) signals, inductive coupling, optical signals, acoustic signals, conducted communication signals, and/or any other signals suitable for communication.

In some cases, as discussed, the communication module 102 may be configured to communicate using two or more different communication modes, in some cases serially while in other cases in parallel. In some cases, for example, the communication module 102 may be configured to communicate using conducted communication by sending and/or receiving communication signals using the electrodes 114 and or 114' of the LCP 100. In some cases, the communication module 102 may be configured to communicate using inductive communication by sending and/or receiving communication signals via one or more inductive coils that may be disposed proximate to and/or disposed within the LCP 100. In some cases, the communication module 102 may be configured to communicate using radio frequency (RF) communication by sending and/or receiving communication signals via one or more RF antennas that may be disposed proximate to and/or disposed within the LCP 100. In some cases, the communication module 102 may be configured to communicate using optical communication by sending and/or receiving communication signals via one or more optical transceivers that may be disposed proximate to and/or disposed within the LCP 100. In some cases, the communication module 102 may be configured to communicate using acoustic communication by sending and/or receiving communication signals via one or more acoustic transceivers that may be disposed proximate to and/or disposed within the LCP 100. These are just examples.

In some cases, the communication module 102 may be configured to switch between communication modes, such as when commanded, at a certain time of day, when a certain posture is detected, when a signal-to-noise ratio (SNR) of an active communication mode falls below a threshold level, when communication errors of an active communication mode exceed a threshold level, during certain times of a respiratory cycle, during certain times of a cardiac cycle, during certain detected activity levels, and/or at any other suitable time or any other suitable detected condition.

In the example shown in FIG. 8, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 8 as separate sensing modules, in some cases, the electrical sensing module 206 and the mechanical sensing module 208 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, such as a super capacitor, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 9:
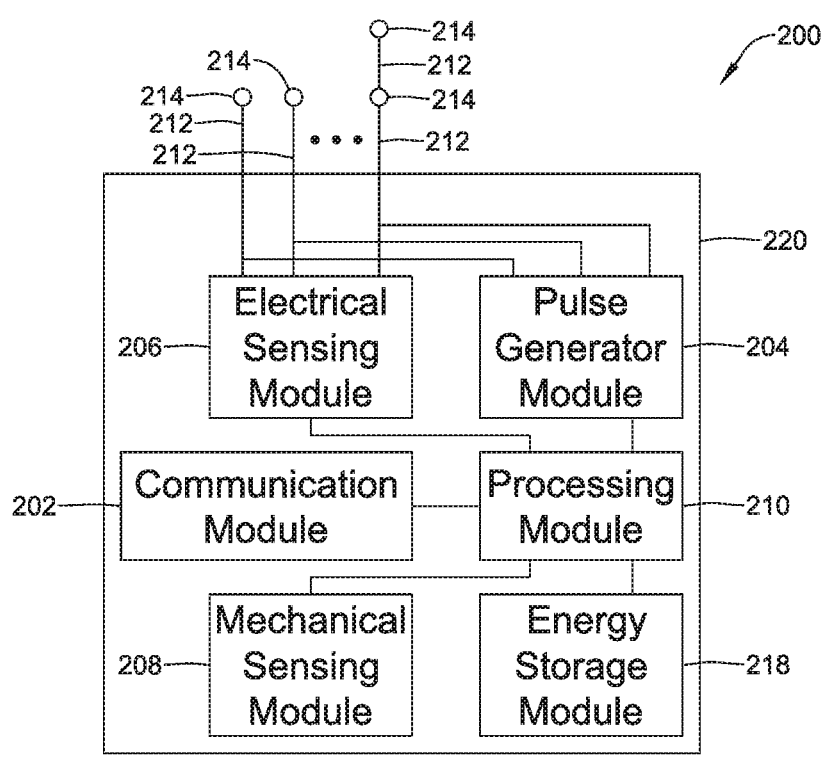
FIG. 9 is a schematic block diagram of another illustrative medical device that may be used in conjunction with the LCP of FIG. 8.

FIG. 9 depicts an example of another or second medical device (MD) 200, which may be used in conjunction with the LCP 100 (FIG. 8) in order to detect and/or treat cardiac abnormalities. In some cases, the MD 200 may be considered as an example of the LCP 20 (FIG. 2), the LCP 40 (FIG. 3) or the LCP 80 (FIG. 6). In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 8, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

In some cases, an implantable medical device such as described herein may include a circuit board (such as but not limited to the circuit board 52 shown in FIG. 3). The circuit board may be planar. In other cases, the circuit board may be formed as two or more distinct circuit boards, or island sections, that are electrically and mechanically connected together via intermediate ribbon sections. In some cases, for example, a stacked circuit board may provide for two or more distinct island sections that are parallel to each other, or at least substantially parallel to each other, once disposed within a medical device housing. It will be appreciated that the stacked island sections may provide suitable locations for disposing one or more inductive coils. FIGS. 10 through 14 provide illustrative but non-limiting examples of stacked circuit board configurations that facilitate placement of one or more inductive coils. Further details regarding the composition and construction of these stacked circuit boards may be found in U.S. Patent Application Publication No. 2016/0151621, the contents of which are hereby incorporated by reference.

Figure 10:
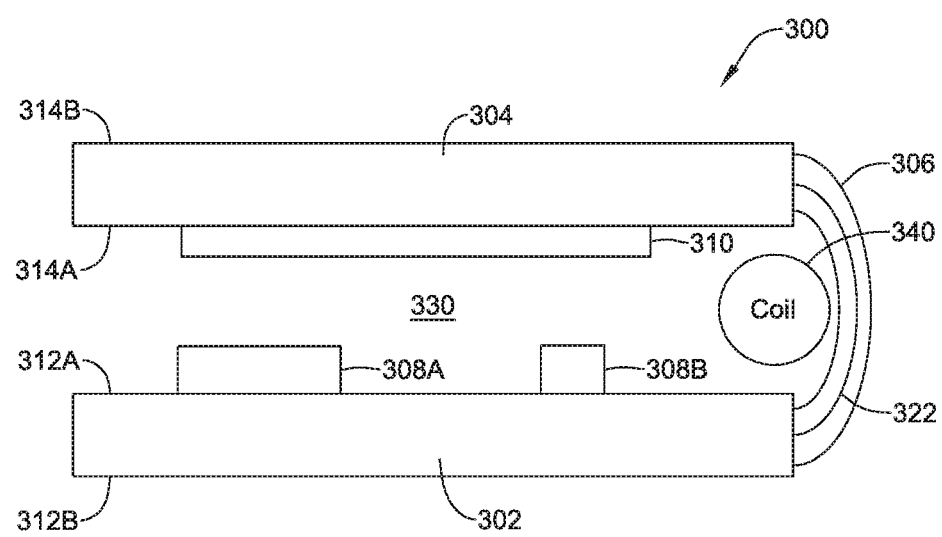
FIG. 10 is an example diagram of an example electrical circuit incorporating an inductive coil in accordance with an example of the disclosure.

In FIG. 10, an electrical circuit 300 includes an island section 302 and an island section 304 that are joined together via a ribbon section 306. A processing module 310 is shown as being fixed to the island section 304 and circuit elements 308A and 308B are shown as being fixed to the island section 302. In one example, the processing module 310 and circuit elements 308A and 308B may represent circuit elements that implement the functions of communication module 102, pulse generator module 104, electrical sensing module 106, mechanical sensing module 108, and/or processing module 110. The processing module 210 may include any circuit elements or components, such as a pre-programmed logic chip or a programmable microprocessor. The circuit elements 308A and 308B may represent capacitors, resistors, diodes, or other circuit elements.

In some cases, an inductive coil 340 may be disposed between the island section 302 and the island section 304, and may extend at least substantially parallel to the island section 302 and the island section 304. As illustrated, the inductive coil 340 may be considered as extending into and out of the page, parallel with the island section 302 and/or the island section 304, such that the inductive coil 340 may be disposed within a device housing in an orientation at least substantially orthogonal to a longitudinal axis of the device housing (see FIG. 14). Substantially orthogonal may be defined, for example, as being orthogonal to or at least within 15 degrees of being orthogonal. The inductive coil 340 may be considered as being an example of the inductive coil 70 shown in FIGS. 5A and 5B, having a length L that is greater than its width W. In some cases, while not illustrated, an electrically inert filler material may be disposed within any space remaining between the island sections 302 and 304. In at least some examples, the filler material may be a desiccant. Some example filler materials include silicone or other inert compounds.

In some examples, each island section 302, 304 may be circular in shape, but this is not required. Each island section 302, 304 may have a diameter that is slightly less than an inner diameter of a cross section of an implantable medical device housing (e.g. LCP 100) so that the island sections 302, 304 may fit within the device when stacked (see FIG. 14). Some example diameters include 3.80 millimeters to 12.7 millimeters. However, in other examples, the islands 302, 304 may be triangular, square, ovular, or any other suitable shape. In at least some examples, the specific shape of the islands sections 302, 304 may generally match a cross section shape of an implantable medical device housing. Some example ranges for the length of the ribbon section 306 include 3.80 millimeters to 12.7 millimeters.

The island sections 302, 304 may include rigid printed circuit boards (PCBs). In such cases, the island sections 302, 304 may include metal or other traces electrically connecting each of the components on each of the island sections 302, 304. The ribbon section 306, on the other hand, may include a flexible substrate, for example a polymer including polyamide or any other suitable flexible substrate. Trace(s) 322 may be embedded within the polymer of the ribbon section 306 and may be electrically insulated from the environment external to the electrical circuit 300. Generally, the ribbon section 306 may be relatively more flexible than the island sections 302, 304. Accordingly, when disposed within an implantable medical device, such as LCP 100, the ribbon section 306 may be folded or bent to allow island sections 302, 304 to be stacked relative to one another without bending the island sections 302, 304 to a significant degree (e.g. less than a 15 degree deflection between two tangent lines, where each tangent line is tangent to the upper surface of the island section at a corresponding edge of the island section).

Figure 11:
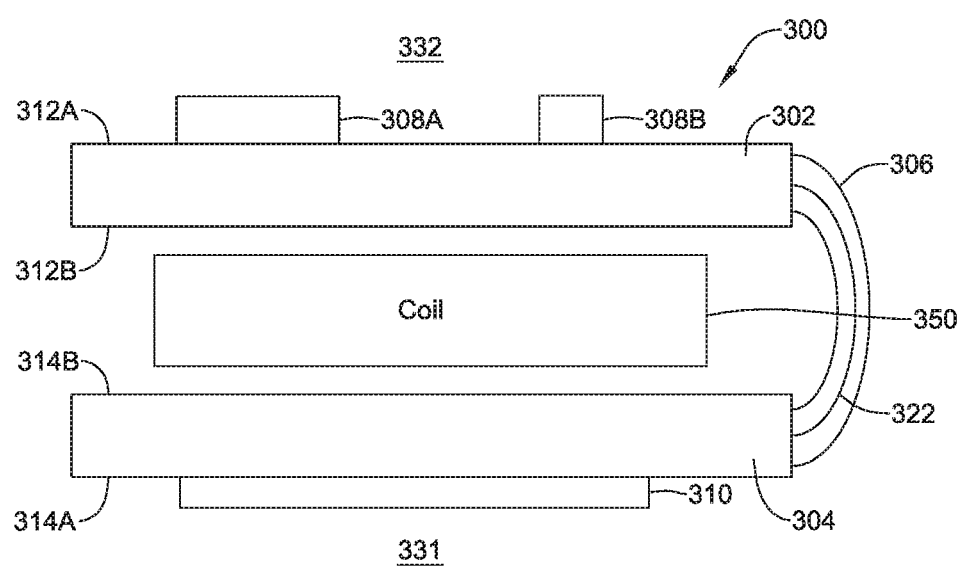
FIG. 11 is an example diagram of an example electrical circuit incorporating an inductive coil in accordance with an example of the disclosure.

FIG. 11 depicts another example configuration of islands 302, 304. In the example of FIG. 11, second major opposing surfaces 312B, 314B are facing each other. With the processing module 310 and the circuit elements 308A-308C in the configuration as depicted in FIG. 11, this means that the processing module 310 and the circuit elements 308A-308C are disposed on the outside of the stacked circuit. In some cases, this arrangement may provide additional space for an inductive coil 350 to be disposed between the island section 302 and the island section 304, and may extend at least substantially parallel to the island section 302 and the island section 304. As illustrated, the inductive coil 350 may be considered as extending lengthwise from left-right on the page, parallel with the island section 302 and/or the island section 304, such that the inductive coil 350 may be disposed within a device housing in an orientation at least substantially orthogonal to a longitudinal axis of the device housing and at least substantially orthogonal to the inductive coil 340 shown in FIG. 10. The inductive coil 350 may be considered as being another example of the inductive coil 70 shown in FIGS. 5A and 5B, having a length L that is greater than its width W. In some cases, while not illustrated, an electrically inert filler material may be disposed within any space remaining between the island sections 302 and 304. In at least some examples, the filler material may be a desiccant. Some example filler materials include silicone or other inert compounds.

Figure 12:
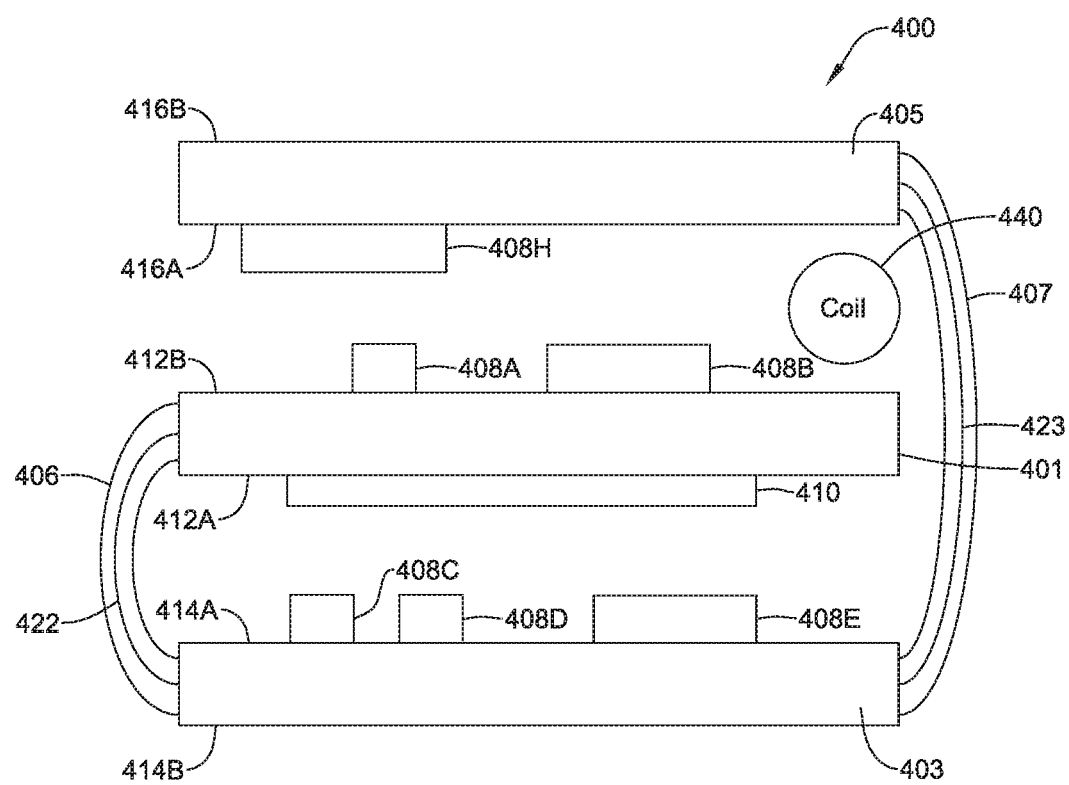
FIG. 12 is an example diagram of an example electrical circuit incorporating an inductive coil in accordance with an example of the disclosure.
Figure 13:
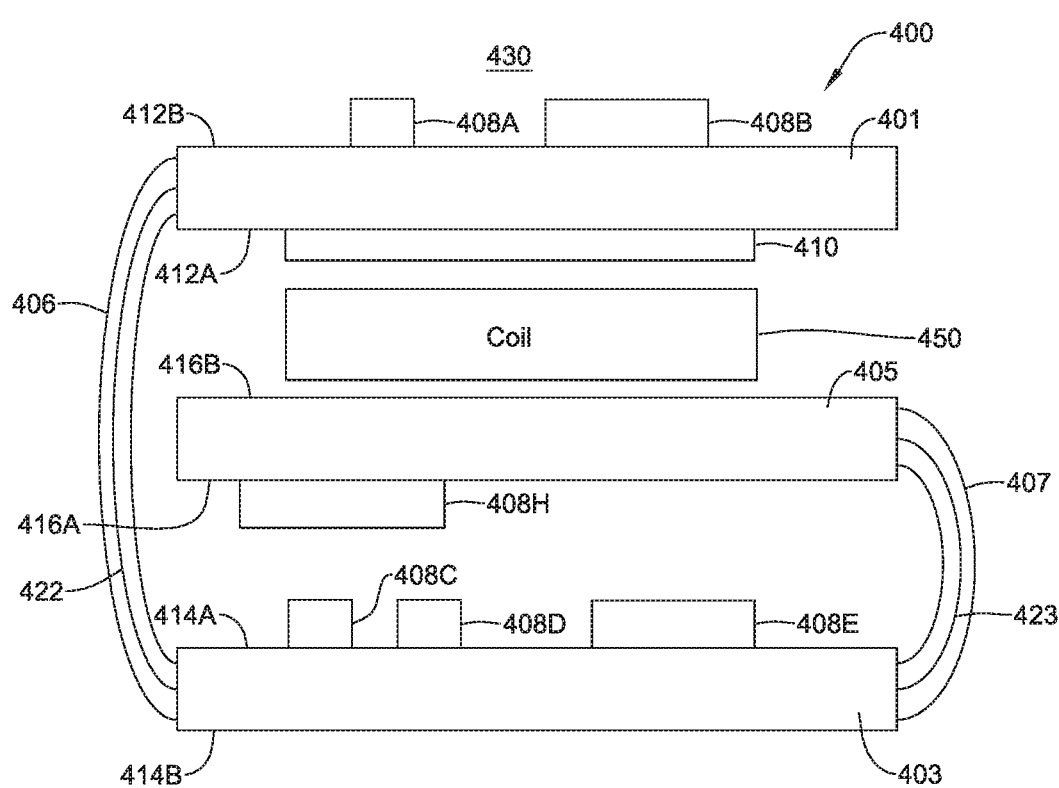
FIG. 13 is an example diagram of an example electrical circuit incorporating an inductive coil in accordance with an example of the disclosure.

FIGS. 12 and 13 provide example configurations of an electrical circuit 400 that may be disposed within an implantable medical device, such as LCP 100, as well as how one or more inductive coils may be fit into and/or around the electrical circuit 400. In FIG. 12, island sections 401, 403, and 405 are stacked with first major opposing surfaces 412A and 414A of the island sections 401 and 403 facing each other and with a second major opposing surface of the island section 401 and a first major opposing surface 416A facing each other.

In some cases, an inductive coil 440 may be disposed between the island section 401 and the island section 405, and may extend at least substantially parallel to the island section 401 and the island section 405. As illustrated, the inductive coil 440 may be considered as extending into and out of the page, parallel with the island section 401 and/or the island section 405, such that the inductive coil 440 may be disposed within a device housing in an orientation at least substantially orthogonal to a longitudinal axis of the device housing (see FIG. 14). The inductive coil 440 may be considered as being another example of the inductive coil 70 shown in FIGS. 5A and 5B, having a length L that is greater than its width W. In some cases, while not illustrated, an electrically inert filler material may be disposed within any space remaining between the island sections 401 and 405, and between the island sections 401 and 403. In at least some examples, the filler material may be a desiccant. Some example filler materials include silicone or other inert compounds.

In FIG. 13, the island sections 401, 403, and 405 are stacked with a first major opposing surface 412A and a second major opposing surface 416B of island sections 401 and 405, respectively, facing each other and with first major opposing surfaces 416A, 412A of the island sections 403, 405 facing each other. In this configuration, the first ribbon section 406 may be longer than the second ribbon section 407.

In some cases, an inductive coil 450 may be disposed between the island section 401 and the island section 405, and may extend at least substantially parallel to the island section 401 and the island section 405. As illustrated, the inductive coil 450 may be considered as extending lengthwise from left-right on the page, parallel with the island section 401 and/or the island section 405, such that the inductive coil 450 may be disposed within a device housing in an orientation at least substantially orthogonal to a longitudinal axis of the device housing. The inductive coil 450 may be considered as being another example of the inductive coil 70 shown in FIGS. 5A and 5B, having a length L that is greater than its width W. In some cases, while not illustrated, an electrically inert filler material may be disposed within any space remaining between the island sections 401 and 405, and between the island sections 401 and 403. In at least some examples, the filler material may be a desiccant. Some example filler materials include silicone or other inert compounds.

Of course, these are only a few examples of stacked configurations that island sections 401, 403, and 405 may take. In other examples, the island section 403 may be in the middle of the stack with the island section 401 on top and the island section 405 on bottom. In still further examples, the locations of the processing module 410 and the circuit elements 408A-H may differ, or the island sections may include additional or different components, e.g. various mechanical/physiological/biological sensors such as an accelerometer, a posture sensor, heart sounds sensor, or the like. Accordingly, the stacked configuration of these different examples may look different than depicted in FIGS. 12 and 13, or the dimensions of the stacked configurations may differ to accommodate the various different components. The relative positions of the one or more inductive coils may be modified to accommodate the particular stacked configuration and needs of the particular medical device.

Figure 14:
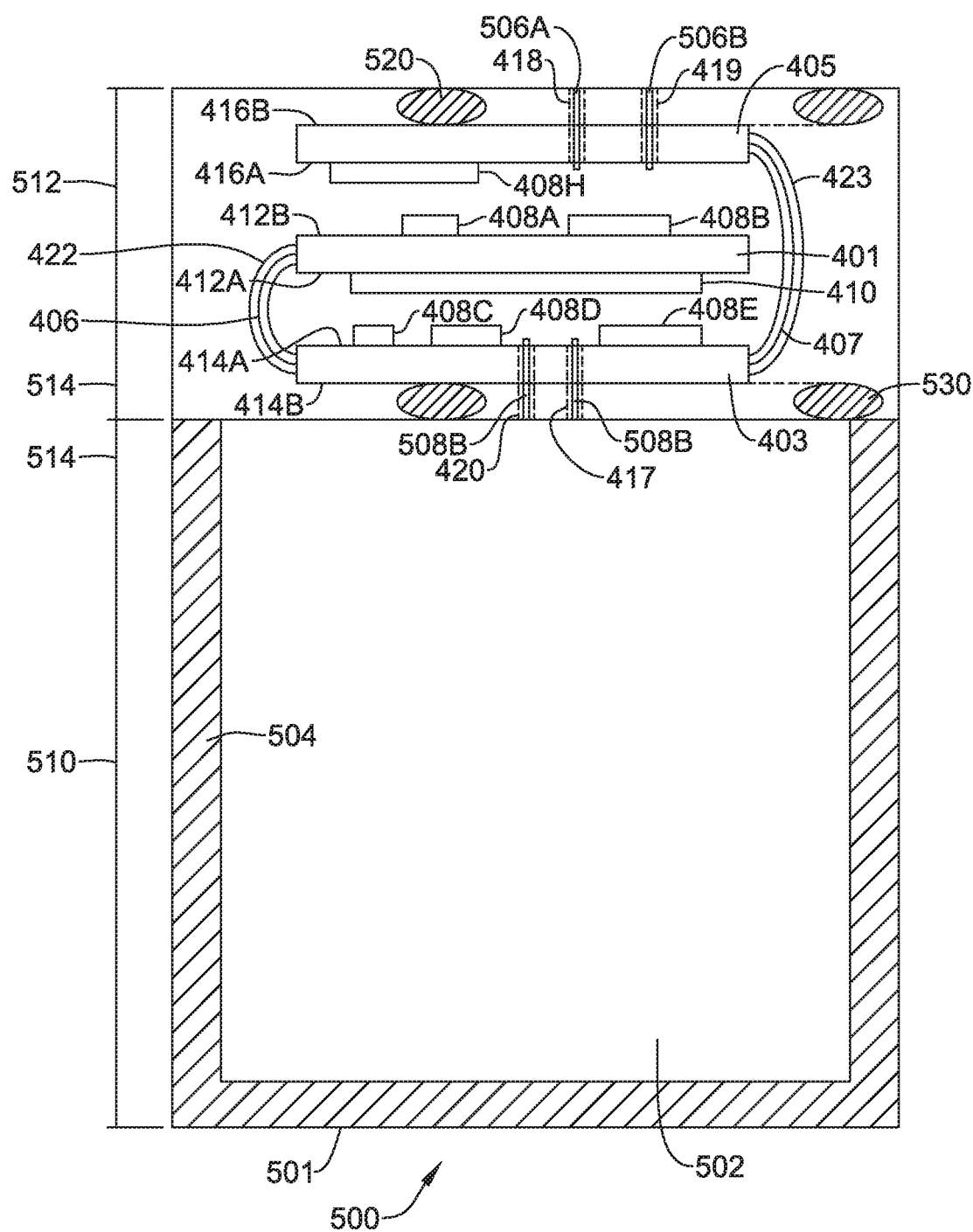
FIG. 14 is a schematic diagram of an illustrative medical device including one or more inductive coils in accordance with an example of the disclosure.

FIG. 14 is an illustrative cross-section of an exemplary implantable medical device with the example circuit 400 in the configuration of FIG. 12 disposed within the implantable medical device. The illustrative implantable medical device 500 may include the circuit 400 along with an energy storage device 502. Both the circuit 400 and the energy storage device 502 may be hermetically sealed within a housing 501. In some examples, the circuit 400 may generally be stacked on top of the energy storage device 502, as illustrated in FIG. 14. Implantable medical device 500 may also include interconnect 506A, 506B and 508A, 508B. The interconnects 506A, 506B may generally extend into or through feedthroughs 418 and 419. The interconnects 506A, 506B may be connected to electrode(s) external to the housing 501 and/or directly to housing 501, thereby electrically connecting the electrode(s) and/or the housing 501 to the circuit 400. The interconnects 508A, 508B may be connected to an electrode, the housing 501, and/or the energy storage device 502, thereby electrically connecting the electrode, the housing 501, and/or the energy storage device 502 to the circuit 400. In some examples, the implantable medical device 500 may further include insulation 504 lining the housing 501 to electrically isolate the energy storage device 502 from the housing 501 and, in some examples, other internal components of the implantable medical device 500.

In some cases, the feedthroughs 418 and 419 may provide a location in which an inductive coil 520 may be disposed. In some cases, the inductive coil 520 may be considered as being an example of the inductive coil 92 shown in FIGS. 7A and 7B, having a length to width ratio that is less than 1. In some cases, the inductive coil 520 may further be considered as being an example of the inductive coil 62 shown in FIG. 4, and the feedthroughs 418 and 419 may be considered as being an example of the internal components 48 that extend at least partially into the inductive coil 62.

Similarly, the feedthroughs 417 and 420 may provide a location in which an inductive coil 530 may be disposed. In some cases, the inductive coil 530 may be considered as being another example of the inductive coil 92 shown in FIGS. 7A and 7B, having a length to width ratio that is less than 1. In some cases, the inductive coil 530 may further be considered as being another example of the inductive coil 62 shown in FIG. 4, and the feedthroughs 417 and 420 may be considered as being another example of the internal components 48 that extend at least partially into the inductive coil 62.

In some cases, it will be appreciated that the implantable medical device 500, which may for example be a leadless cardiac pacemaker (LCP), may include either the inductive coil 520 or the inductive coil 530, or both. In some cases, the implantable medical device 500 may include one or more of the inductive coils 340, 350, 440 and 450 as shown in FIGS. 10 through 13 in combination with one or more of the inductive coil 520 and the inductive coil 530. In some cases, the use of multiple inductive coils, arranged in different relative orientations, may be useful in minimizing the impact of the spatial and/or temporal nulls that any one inductive coil may have.

The implantable medical device 500 may generally have a length 514 as illustrated in FIG. 14. When measuring along this length dimension, the energy storage device 502 may extend for a length 510 and the circuit 400 may extend for a length 512. Some example values for the length 510 may range from five millimeters to twenty-five millimeters, and in some examples the length 510 may be fourteen millimeters. Some example values for the length 512 may range from one millimeter to five millimeters, and in some examples the length 512 may be two millimeters. Percentages may be another way to describe the relative portions of the implantable medical device 500 that the circuit 400 and the energy storage device 502 take up.

For instance, the length that the energy storage device 502 extends within implantable medical device 500 may be between fifty percent and ninety-five percent of the total length of the implantable medical device 500, or the length 514. In some examples, the energy storage device 502 may extend within the implantable medical device 500 for eighty percent of the length 512. Additionally, the length that the circuit 400 may extend within the implantable medical device 500 may be between five percent and fifty percent of the length 514. In some additional examples, the circuit 400 may extend within the implantable medical device 500 for twenty percent of the length 514. Although FIG. 14 is depicted with the circuit 400 disposed within implantable medical device 500, along with the inductive coils 520, 530, in other examples the implantable medical device 500 may include the circuit 300 disposed within the housing 501 and stacked on top of the energy storage device 502.

Figure 15:
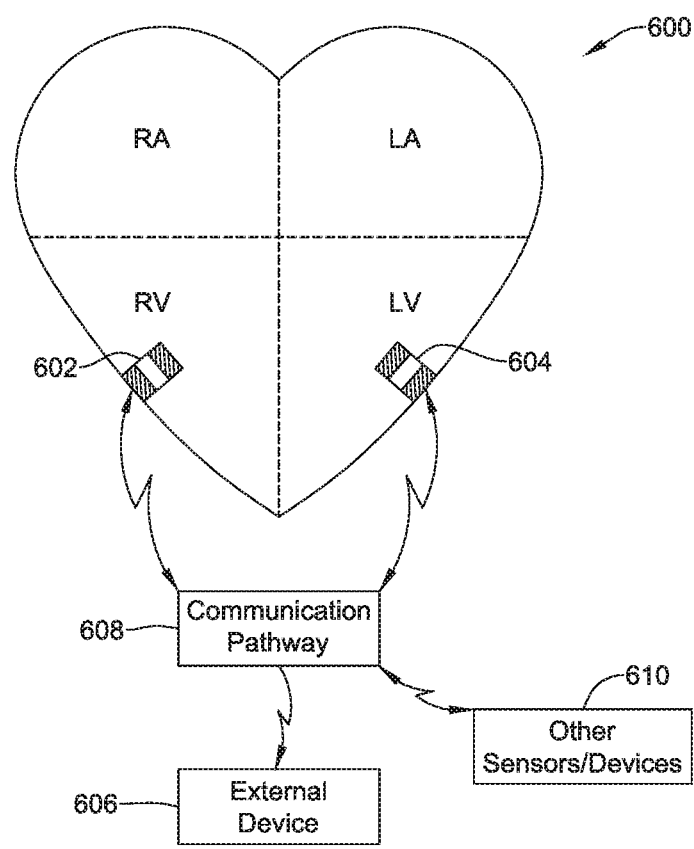
FIG. 15 is a schematic diagram of an exemplary medical system that includes multiple LCPs and/or other devices in communication with one another.

FIG. 15 illustrates an example of a medical device system and a communication pathway through which multiple medical devices 602, 604, 606, and/or 610 may communicate. In the example shown, the medical device system 600 may include LCPs 602 and 604, external medical device 606, and other sensors/devices 610. The external device 606 may be any suitable device. In some cases, external device 606 may include an external programmer device. Other sensors/devices 610 may also be any suitable device or devices. In some instances, other sensors/devices 610 may include a sensor, such as an accelerometer, an acoustic sensor, a blood pressure sensor, or the like. In some cases, other sensors/devices 610 may include an external programmer device that may be used to program one or more devices of the system 600.

Various devices of the system 600 may communicate via communication pathway 608. For example, the LCPs 602 and/or 604 may sense intrinsic cardiac electrical signals and may communicate such signals to one or more other devices 602/604, 606, and 610 of the system 600 via communication pathway 608. In one example, one or more of the devices 602/604 may receive such signals and, based on the received signals, determine an occurrence of an arrhythmia. In some cases, the device or devices 602/604 may communicate such determinations to one or more other devices 606 and 610 of the system 600. In some cases, one or more of the devices 602/604, 606, and 610 of the system 600 may take action based on the communicated determination of an arrhythmia, such as by delivering a suitable electrical stimulation to the heart of the patient. It is contemplated that the communication pathway 608 may communicate using conducted communication, inductive communication, RF communication, optical communication, acoustic communication, or any other suitable communication mode. In some cases, the communication pathway 608 may switch between communication modes depending on circumstances.

In some cases, the communication pathway 608 may include conducted communication. Accordingly, devices of the system 600 may have components that allow for such conducted communication. For instance, the devices of system 600 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 600. In such examples, the delivered conducted communication signals (e.g. pulses) may differ from pacing or other therapy signals. For example, the devices of the system 600 may deliver electrical communication pulses at an amplitude/pulse width that is sub-capture threshold to the heart. Although, in some cases, the amplitude/pulse width of the delivered electrical communication pulses may be above the capture threshold of the heart, but may be delivered during a blanking period of the heart (e.g. refractory period) and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 16:
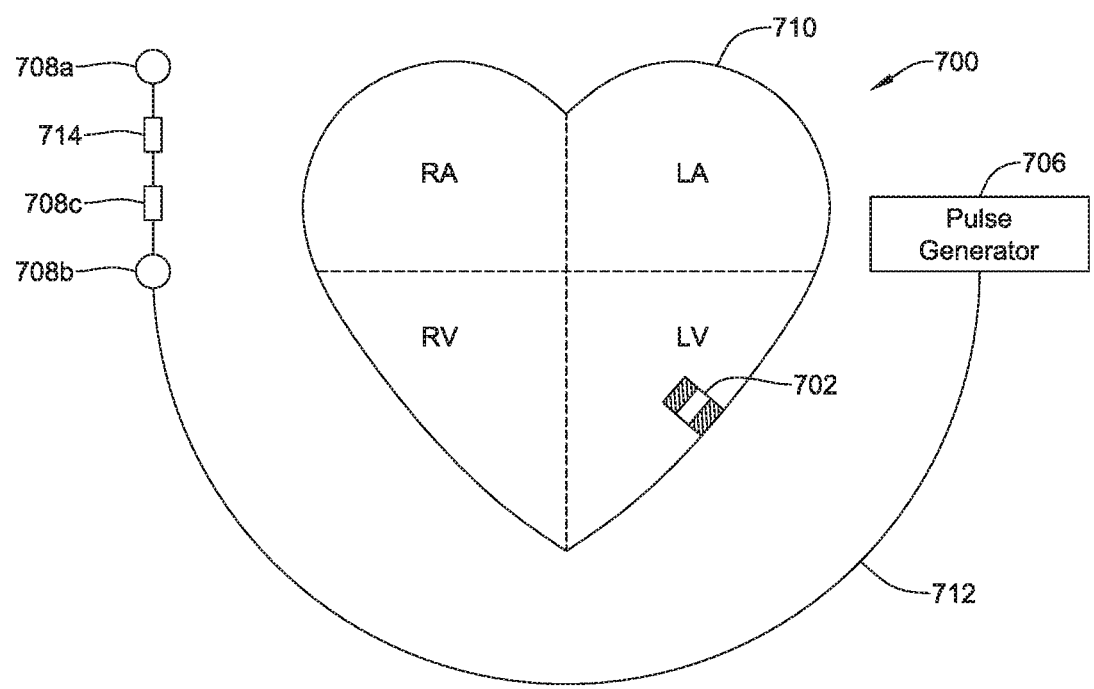
FIG. 16 is a schematic diagram of a system including an LCP and another medical device, in accordance with an example of the disclosure.

FIG. 16 shows an illustrative medical device system. In FIG. 16, an LCP 702 is shown fixed to the interior of the left ventricle of the heart 710, and a pulse generator 706 is shown coupled to a lead 712 having one or more electrodes 708a-708c. In some cases, the pulse generator 706 may be part of a subcutaneous implantable cardioverter-defibrillator (S-ICD), and the one or more electrodes 708a-708c may be positioned subcutaneously. In some cases, the one or more electrodes 708a-708c may be placed inside of the chest cavity but outside of the heart, such as just interior of the sternum.

In some cases, the LCP 702 may communicate with the subcutaneous implantable cardioverter-defibrillator (S-ICD). In some cases, the lead 712 and/or pulse generator 706 may include an accelerometer 714 that may, for example, be configured to sense vibrations that may be indicative of heart sounds.

In some cases, the LCP 702 may be in the right ventricle, right atrium, left ventricle or left atrium of the heart, as desired. In some cases, more than one LCP 702 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart. The LCP 702 and the pulse generator 706 may be configured to communicate using two or more different communication modes, such as conducted communication and inductive communication. In some cases, the LCP 702 and the pulse generator 706 may be configured to switch communication mode types, depending on the circumstances.

Figure 17:
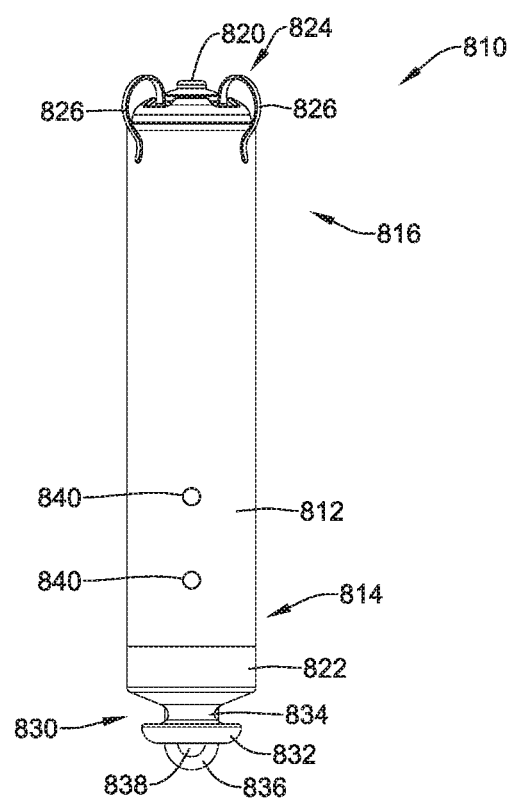
FIG. 17 is a side view of an illustrative implantable leadless cardiac device.

FIG. 17 is a side view of an illustrative implantable leadless cardiac pacemaker (LCP) 810. In some cases, the LCP 810 may incorporate one or more inductive coils, in order to facilitate inductive communication, as discussed with respect to previous Figures. The LCP 810 may be similar in form and function to the LCP 100 described above. The LCP 810 may include any of the modules and/or structural features described above with respect to the LCP 100 described above. The LCP 810 may include a shell or housing 812 having a proximal end 814 and a distal end 816. The illustrative LCP 810 includes a first electrode 820 secured relative to the housing 812 and positioned adjacent to the distal end 816 of the housing 812 and a second electrode 822 secured relative to the housing 812 and positioned adjacent to the proximal end 814 of the housing 812. In some cases, the housing 812 may include a conductive material and may be insulated along a portion of its length. A section along the proximal end 814 may be free of insulation so as to define the second electrode 822. The electrodes 820, 822 may be sensing and/or pacing electrodes to provide electro-therapy and/or sensing capabilities. The first electrode 820 may be capable of being positioned against or may otherwise contact the cardiac tissue of the heart while the second electrode 822 may be spaced away from the first electrode 820. The first and/or second electrodes 820, 822 may be exposed to the environment outside the housing 812 (e.g. to blood and/or tissue).

In some cases, the LCP 810 may include a pulse generator (e.g., electrical circuitry) and a power source (e.g., a battery) within the housing 812 to provide electrical signals to the electrodes 820, 822 to control the pacing/sensing electrodes 820, 822. While not explicitly shown, the LCP 810 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 812. Electrical connections between the pulse generator and the electrodes 820, 822 may allow electrical stimulation to heart tissue and/or sense a physiological condition.

In the example shown, the LCP 810 includes a fixation mechanism 824 proximate the distal end 816 of the housing 812. The fixation mechanism 824 is configured to attach the LCP 810 to a wall of the heart H, or otherwise anchor the LCP 810 to the anatomy of the patient. In some instances, the fixation mechanism 824 may include one or more, or a plurality of hooks or tines 826 anchored into the cardiac tissue of the heart H to attach the LCP 810 to a tissue wall. In other instances, the fixation mechanism 824 may include one or more, or a plurality of passive tines, configured to entangle with trabeculae within the chamber of the heart H and/or a helical fixation anchor configured to be screwed into a tissue wall to anchor the LCP 810 to the heart H. These are just examples.

The LCP 810 may further include a docking member 830 proximate the proximal end 814 of the housing 812. The docking member 830 may be configured to facilitate delivery and/or retrieval of the LCP 810. For example, the docking member 830 may extend from the proximal end 814 of the housing 812 along a longitudinal axis of the housing 812. The docking member 830 may include a head portion 832 and a neck portion 834 extending between the housing 812 and the head portion 832. The head portion 832 may be an enlarged portion relative to the neck portion 834. For example, the head portion 832 may have a radial dimension from the longitudinal axis of the LCP 810 that is greater than a radial dimension of the neck portion 834 from the longitudinal axis of the LCP 810. In some cases, the docking member 630 may further include a tether retention structure 836 extending from or recessed within the head portion 832. The tether retention structure 836 may define an opening 838 configured to receive a tether or other anchoring mechanism therethrough. While the retention structure 836 is shown as having a generally "U-shaped" configuration, the retention structure 836 may take any shape that provides an enclosed perimeter surrounding the opening 838 such that a tether may be securably and releasably passed (e.g. looped) through the opening 838. In some cases, the retention structure 836 may extend though the head portion 832, along the neck portion 834, and to or into the proximal end 814 of the housing 812. The docking member 830 may be configured to facilitate delivery of the LCP 810 to the intracardiac site and/or retrieval of the LCP 810 from the intracardiac site. While this describes one example docking member 830, it is contemplated that the docking member 830, when provided, can have any suitable configuration.

It is contemplated that the LCP 810 may include one or more pressure sensors 840 coupled to or formed within the housing 812 such that the pressure sensor(s) is exposed to the environment outside the housing 812 to measure blood pressure within the heart. For example, if the LCP 810 is placed in the left ventricle, the pressure sensor(s) 840 may measure the pressure within the left ventricle. If the LCP 810 is placed in another portion of the heart (such as one of the atriums or the right ventricle), the pressures sensor(s) may measure the pressure within that portion of the heart. The pressure sensor(s) 840 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 840 may be part of a mechanical sensing module described herein. It is contemplated that the pressure measurements obtained from the pressures sensor(s) 840 may be used to generate a pressure curve over cardiac cycles. The pressure readings may be taken in combination with impedance measurements (e.g. the impedance between electrodes 820 and 822) to generate a pressure-impedance loop for one or more cardiac cycles. The impedance may be a surrogate for chamber volume, and thus the pressure-impedance loop may be representative for a pressure-volume loop for the heart H.

In some embodiments, the LCP 810 may be configured to measure impedance between the electrodes 820, 822. More generally, the impedance may be measured between other electrode pairs, such as the additional electrodes 114' described above. In some cases, the impedance may be measure between two spaced LCP's, such as two LCP's implanted within the same chamber (e.g. LV) of the heart H, or two LCP's implanted in different chambers of the heart H (e.g. RV and LV). The processing module of the LCP 810 and/or external support devices may derive a measure of cardiac volume from intracardiac impedance measurements made between the electrodes 820, 822 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 810 may be provided with energy delivery circuitry operatively coupled to the first electrode 820 and the second electrode 822 for causing a current to flow between the first electrode 820 and the second electrode 822 in order to determine the impedance between the two electrodes 820, 822 (or other electrode pair). It is contemplated that the energy delivery circuitry may also be configured to deliver pacing pulses via the first and/or second electrodes 820, 822. The LCP 810 may further include detection circuitry operatively coupled to the first electrode 820 and the second electrode 822 for detecting an electrical signal received between the first electrode 820 and the second electrode 822. In some instances, the detection circuitry may be configured to detect cardiac signals received between the first electrode 820 and the second electrode 822.

When the energy delivery circuitry delivers a current between the first electrode 820 and the second electrode 822, the detection circuitry may measure a resulting voltage between the first electrode 820 and the second electrode 822 (or between a third and fourth electrode separate from the first electrode 820 and the second electrode 822, not shown) to determine the impedance. When the energy delivery circuitry delivers a voltage between the first electrode 820 and the second electrode 822, the detection circuitry may measure a resulting current between the first electrode 820 and the second electrode 822 (or between a third and fourth electrode separate from the first electrode 820 and the second electrode 822) to determine the impedance.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A leadless cardiac pacemaker (LCP) configured to pace a patient's heart, the LCP disposable within a chamber of the patient's heart, the LCP comprising:
    a housing;
    a plurality of electrodes secured relative to the housing;
    two or more inductive coils secured relative to the housing, wherein each of the two or more inductive coils includes a plurality of windings extending about a central axis, wherein the central axis of one of the two or more inductive coils is not coaxial and not parallel with the central axis of another one of the two or more inductive coils;
    a controller disposed within the housing and operably coupled to the plurality of electrodes and the two or more inductive coils, the controller configured to sense cardiac electrical activity of the patient's heart via two or more of the electrodes and to generate and deliver pacing pulses via two or more of the electrodes; and
    the controller is configured to communicate information between the LCP and one or more remotely located devices using:
        conducted communication via two or more of the electrodes; and
        inductive communication via one or more of the two or more inductive coils.

2. The LCP of claim 1, wherein the controller is configured to select a particular one of the two or more inductive coils for inductive communication, and to communicate information with one or more remotely located devices using inductive communication via the selected one of the two or more inductive coils, while not using the non-selected ones of the two or more inductive coils for inductive communication.

3. The LCP of claim 1, wherein the controller is configured to select two or more of the inductive coils for inductive communication, and to communicate information with one or more remotely located devices using inductive communication via the selected two or more inductive coils.

4. The LCP of claim 1, wherein at least one of the two or more inductive coils is disposed within the housing.

5. The LCP of claim 1, wherein the controller is configured to:
    disable inductive communication to save power;
    communicate information with one or more remotely located devices using conducted communication;
    detect a predetermined condition, and in response to detecting the predetermined condition, enable inductive communication and communicate information with one or more remotely located devices using inductive communication.

6. The LCP of claim 5, wherein the controller includes a time clock, and the predetermined condition comprises a predetermined time of day.

7. The LCP of claim 5, wherein the LCP further includes a posture sensor for detecting a posture of the patient, and the predetermined condition comprises detection of a predetermined posture of the patient.

8. The LCP of claim 5, wherein the predetermined condition comprises an error in conducted communication with one or more remotely located devices.

9. The LCP of claim 1, wherein the controller is further configured to have a fail-safe in which a user is prevented from having conductive communication and inductive communication disabled at the same time.

10. A leadless cardiac pacemaker (LCP) configured to pace a patient's heart, the LCP disposable within a chamber of the patient's heart, the LCP comprising:
- an elongated housing having a length dimension and a width dimension, wherein the length dimension is longer than the width dimension;
- a plurality of electrodes secured relative to the elongated housing;
- a plurality of internal components within the elongated housing, the plurality of internal components comprising:
  - an inductive coil disposed within the elongated housing, the inductive coil comprising a plurality of windings extending about a central aperture, wherein the central aperture of the inductive coil is aligned in the direction of the length dimension of the elongated housing;
  - a circuit board including circuitry that is operably coupled to the plurality of electrodes and is configured to sense cardiac electrical activity of the patient's heart via two or more of the electrodes and to generate and deliver pacing pulses via two or more of the electrodes, the circuitry is further configured to communicate information between the LCP and one or more remotely located devices using:
    - conducted communication via two or more of the electrodes; and
    - inductive communication via the inductive coil;
  - a battery disposed within the elongated housing and operably coupled to the circuitry; and
- wherein at least part of one or more of the internal components of the LCP extends into and occupies at least part of the central aperture of the inductive coil.

11. The LCP of claim 10, wherein the inductive coil has a length extending along the length dimension of the elongated housing and a width orthogonal to the length, wherein a ratio of the length of the inductive coil to the width is less than one.

12. The LCP of claim 10, wherein the plurality of internal components within the elongated housing comprises a battery pin extending between a terminal of the battery and circuitry of the circuit board, wherein the battery pin extends through the occupies at least part of the central aperture of the inductive coil.

13. The LCP of claim 10, wherein the plurality of internal components within the elongated housing comprises a feed through pin extending between circuitry of the circuit board and one of the plurality of electrodes, wherein the feed through pin extends through and occupies at least part of the central aperture of the inductive coil.

14. The LCP of claim 10, further comprising a second inductive coil that is disposed within the elongated housing, the second inductive coil comprising a plurality of windings extending about a central aperture, wherein the central aperture of the second inductive coil extends in the direction of the width dimension of the elongated housing.

15. The LCP of claim 14, wherein the central aperture of the second inductive coil extends parallel with the circuit board or perpendicular to the circuit board.

16. The LCP of claim 14, wherein the second inductive coil has a length that extends in the direction of the width dimension of the elongated housing, and a width that is orthogonal to the length, wherein a ratio of the length of the inductive coil to the width is greater than three, and wherein the second inductive coil comprises a ferrite core in the central aperture of the second inductive coil.

17. A leadless cardiac pacemaker (LCP) configured to pace a patient's heart, the LCP disposable within a chamber of the patient's heart, the LCP comprising:
- an elongated housing having a length dimension and a width dimension, wherein the length dimension is longer than the width dimension;
- a plurality of electrodes secured relative to the elongated housing;
- a circuit board assembly including two or more stacked circuit boards operably coupled together via flexible interconnects, the circuit board assembly disposed within the elongated housing such that each of the two or more stacked circuit boards are orthogonal to the length dimension of the elongated housing;
- the circuit board assembly including circuitry that is operably coupled to the plurality of electrodes and is configured to sense cardiac electrical activity of the patient's heart via two or more of the electrodes and to generate and deliver pacing pulses via two or more of the electrodes;
- an inductive coil disposed within the elongated housing such that the inductive coil extends between a first circuit board and a second circuit board of the plurality of circuit boards; and
- the circuitry is configured to communicate information between the LCP and one or more remotely located devices using:
  - conducted communication via two or more of the electrodes; and
  - inductive communication via the inductive coil.

18. The LCP of claim 17, further comprising a second inductive coil disposed within the elongated housing such that the second inductive coil extends between two of the plurality of circuit boards of the plurality of circuit boards.

19. The LCP of claim 17, further comprising a second inductive coil disposed within the elongated housing and arranged orthogonal to the inductive coil.

20. The LCP of claim 19, further comprising a third inductive coil disposed within the elongated housing and arranged orthogonal to both the inductive coil and the second inductive coil.

* * * * *